US008802393B2

(12) United States Patent
Kim et al.

(10) Patent No.: US 8,802,393 B2

(45) Date of Patent: Aug. 12, 2014

(54) **ARABINOSE ISOMERASE EXPRESSED FROM *CORYNEBACTERIUM* GENUS AND TAGATOSE MANUFACTURING METHOD BY USING IT**

(75) Inventors: Seong-bo Kim, Seoul (KR); Young-mi Lee, Seoul (KR); Seung-won Park, Gyeonggi-do (KR); Jung-hoon Kim, Seoul (KR); Sang-hoon Song, Incheon (KR); Kang-pyo Lee, Seoul (KR); Hye-won Kim, Gyeonggi-do (KR); Hye-jin Choi, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 271 days.

(21) Appl. No.: 12/253,454

(22) Filed: Oct. 17, 2008

(65) Prior Publication Data

US 2009/0246828 A1 Oct. 1, 2009

Related U.S. Application Data

(62) Division of application No. 11/564,934, filed on Nov. 30, 2006, now abandoned.

(30) Foreign Application Priority Data

Nov. 27, 2006 (KR) ........................ 10-2006-0117795

(51) Int. Cl.

| | |
|---|---|
| ***C12P 21/06*** | (2006.01) |
| ***C12P 19/00*** | (2006.01) |
| ***C12P 19/20*** | (2006.01) |
| ***C12N 9/00*** | (2006.01) |
| ***C12N 9/92*** | (2006.01) |
| ***C12N 1/20*** | (2006.01) |
| ***C12N 15/00*** | (2006.01) |
| ***C07H 21/04*** | (2006.01) |

(52) U.S. Cl.

USPC .............. 435/69.1; 435/72; 435/94; 435/183; 435/234; 435/252.32; 435/320.1; 536/23.2

(58) Field of Classification Search

None

See application file for complete search history.

(56) References Cited

U.S. PATENT DOCUMENTS

2003/0129710 A1 7/2003 Hansen et al.

FOREIGN PATENT DOCUMENTS

| | | | |
|---|---|---|---|
| KR | 99-16118 | | 5/1999 |
| KR | 10-2002-0051835 | | 6/2002 |
| KR | 10-0443865 | | 7/2004 |
| KR | 10-2006-0068505 | | 6/2006 |
| WO | 02/052021 | | 7/2002 |
| WO | WO-2006-065095 | * | 6/2006 |
| WO | 2008/066280 | | 6/2008 |

OTHER PUBLICATIONS

Whisstock et al. Quaterly Reviews of Biophysics, 2003, “Prediction of protein function from protein sequence and structure”, 36(3): 307-340.*

Chica et al. Semi-rational approaches to engineering enzyme activity: combining the benefits of directed evolution and rational design, Curr Opin Biotechnol. Aug. 2005;16(4):378-84. Review.*

Witkowski et al. Conversion of a beta-ketoacyl synthase to a malonyl decarboxylase by replacement of the active-site cysteine with glutamine, Biochemistry. Sep. 7, 1999;38(36):11643-50.*

Srivastava et al. Gene expression systems in Corynebacteria, Protein Expr Purif. Apr. 2005;40(2):221-9, Review.*

Accession No. AAK18729 GI:19879240 of NCBI database (published Apr. 1, 2000).

Kim et al. FEMS Microbiology Letters, 2002, 212: 121-126.

Branden et al. Introduction to protein structure, Gerald Publishing Inc., New York, p. 247, 1991.

Witkowski et al., Conversion of a beta-ketoacyl synthase to a malonyl decarboxylase by replacement of the active-site cysteine with glutamine, Biochemistry, Sep. 7, 1999; 38(36): 11643-50.

Seffernick et al., Melamine deaminase and atrazine chlorohydrolase: 98 percent identical but functionally different, J Bacteriol. Apr. 2001; 183 (8): 2405-10.

Lee, S.J., et al. Characterization of a Thermoacidophilic L-Arabinose Isomerase from *Alicyclobacillus acidocaldarius*: Role of Lys-269 in pH Optimum.

Office Action in connection with New Zealand application No. 576797 dated Jul. 23, 2010, 7 pages.

Kim, Pil. “Current studies on biological tagatose production using L-arabinose isomerase: a review and future perspective.” Applied Microbiol Biotechnol (2004) 65: pp. 243-249.

Chinese Office Action issued in Application No. 20078004400.X dated Nov. 3, 2010, 4 pages.

* cited by examiner

*Primary Examiner* — Iqbal H Chowdhury

(74) *Attorney, Agent, or Firm* — Occhiuti & Rohlicek LLP

(57) ABSTRACT

The present invention relates to a thermophilic arabinose isomerase and a method of manufacturing tagatose using the same, and more precisely, a gene encoding arabinose isomerase originating from the thermophile *Thermotoga neapolitana* DSM 5068, a recombinant expression vector containing the gene, a method of preparing a food grade thermophilic arabinose isomerase from the recombinant GRAS (Generally Recognized As Safe) strain transformed with the said expression vector, and a method of preparing tagatose from galactose using the said enzyme.

3 Claims, 4 Drawing Sheets

ARABINOSE ISOMERASE EXPRESSED FROM *CORYNEBACTERIUM* GENUS AND TAGATOSE MANUFACTURING METHOD BY USING IT

This application is a divisional of U.S. application Ser. No. 11/564,934, filed Nov. 30, 2006, which claims priority to Korean Application No. 10-2006-0117795, filed Nov. 27, 2006. The content of the application is incorporated by reference in its entirety.

TECHNICAL FIELD

The present invention relates to an arabinose isomerase gene expressed in a *Corynebacterium* sp. strain and a method of preparing tagatose using the same, and more particularly, the present invention provides a gene encoding arabinose isomerase originating from *Thermotoga neapolitana* DSM 5068, a recombinant expression vector containing the gene, a method of preparing a thermophilic arabinose isomerase by expressing the gene in a food grade GRAS *Corynebacterium* sp. strain transfected with the recombinant expression vector, and a method of preparing tagatose from galactose using the same.

BACKGROUND ART

With the increasing interest in well-being or a healthy life, tagatose has been proposed as an alternative to sugar as it has less side effects and sugar is one of the major factors causing various adult diseases. Tagatose is the isomer of galactose and is known to have fructose-like physiochemical properties. Tagatose is a natural low-calorie sugar, and has recently been approved by the FDA in the USA as GRAS (Generally Recognized As Safe), so it is now allowed to be added as a sweetener to foods, beverages, health foods, diet additives, etc.

GRAS indicates a substance that is generally recognized as safe, which is judged by specialized people having enough experience and skills through scientific procedure and examination under the indicated conditions and purpose of use. GRAS is a unique system used only in the USA to evaluate the safety of foods and food chemical substances (under certain conditions) but it is recognized world-wide.

Tagatose is produced by either isomerization, which is a chemical method using a catalyst to produce an isomer, of galactose or a biological method using isomerase to convert galactose enzymatically.

One of the biological methods well-known to those in the art is to convert aldose or aldose derivatives into ketose or ketose derivatives by using an enzyme. The isomerization of galactose to tagatose by using arabinose isomerase is generally carried out thermodynamically at high temperature and exhibits a proportionally high conversion rate. Therefore, developing an enzyme that works stably at high temperature and a method of preparing tagatose using the same are key techniques for the industrial application thereof based on the biological conversion of tagatose using an isomerase. By screening thermophilic bacteria derived arabinose isomerases, an industrially applicable thermophilic isomerase has been tried, and efforts have also been made by many research teams to establish an isomerization process using the same.

In Korea, an enzymatic isomerization method using arabinose isomerase has been developed by Tong Yang Confectionery Corp. According to the method, the arabinose isomerase derived from *E. coli* was homogeneously expressed in *E. coli* by recombinant technology. This recombinant isomerase was reacted at 30° C. for 24 hours to convert galactose into tagatose, and at this time the conversion rate was 25%, indicating that both thermostability and conversion yield were very low (Korean Patent Application No. 99-16118). Professor Oh, Deok-keun and his colleagues (Sejong University) succeeded in heterogeneous expression of arabinose isomerase originating from *Geobacillus stearothermophilus* in *E. coli* and based on that they proposed an isomerization procedure at high temperature to convert galactose into tagatose. The present inventors succeeded in cloning a novel arabinose isomerase gene from *Thermotoga neapolitana* and producing it in *E. coli*, and further developed a method of manufacturing tagatose at hyper-thermophilic condition using the enzyme (Korean Patent No. 10-0443865).

The production of tagatose using a derived arabinose isomerase derived from thermophiles still depends on the method of using a recombinant enzyme mass-expressed in recombinant *E. coli* or the isomerization of galactose to tagatose using a host containing the recombinant enzyme. However, this biological production of tagatose using recombinant *E. coli* is not appropriate for the production of tagatose as a food ingredient. To produce tagatose as a food additive, arabinose isomerase expressed in a host which is a GRAS microorganism appropriate for the mass-production of the same is essential.

*Corynebacterium* is an industrial microorganism that has been used for the production of chemical compounds applicable to a variety of fields including L-lysine, L-threonine and various nucleic acid containing feeds, medical supplies and foods. The *Corynebacterium* is a GRAS (Generally Recognized As Safe) strain, which favors gene manipulation and mass production. In addition, this strain is highly stable under the various process conditions and has a comparatively stable cell membrane, compared with other bacteria. Thus, this strain remains stable even under high osmotic pressure generated by a high concentration of galactose.

The present inventors found that thermophilic arabinose isomerase originating from the hyperthermophile *Thermotoga neapolitana* is overexpressed as an active form in a GRAS *Corynebacterium* sp. strain, and further completed this invention by developing a novel art to induce tagatose isomerization from the high concentration of galactose by using the expressed recombinant enzymes from *Corynebacterium* species.

DISCLOSURE OF THE INVENTION

It is an object of the present invention to provide a method of preparing GRAS strains expressing arabinose isomerase stably in their cells under the conditions of high temperature and high concentration of galactose by taking advantage of mass-production of the recombinant enzyme in the *Corynebacterium* sp. strain.

To overcome the limits of the conventional method in which an enzyme could be expressed only in *E. coli*, it is also an object of the present invention to provide a method of preparing tagatose in which arabinose isomerase originating from *Thermotoga* is expressed as an active form in a GRAS *Corynebacterium* strain, and accordingly food grade tagatose is generated from galactose using the expressed recombinant enzyme or hosts containing the same.

The above object and other objects of the present invention can be achieved by the following embodiments of the present invention.

Hereinafter, the present invention is described in detail.

The present invention provides a method for producing a recombinant enzyme by introducing an arabinose isomerase gene from a microorganism which is very difficult to obtain from a direct cell culture, because the optimum growth conditions for the microorganism is at least 80° C. or are anaerobic conditions, into a food grade host and a method of producing tagatose from galactose using the same.

The arabinose isomerase preferably originates from *Thermotoga* sp., *Thermus* sp. or *Sulforobus* sp. strain whose optimum reaction temperature is in the range of 70~90° C.

The arabinose isomerase gene of the present invention preferably originates from a hyperthermophile and more preferably from the hyperthermophile *Thermotoga neapolitana* DSM 5068, which has the amino acid sequence represented by SEQ. ID. NO: 3.

The arabinose isomerase gene of the present invention can be modified by those in the art using any conventional mutagenesis method such as directed evolution and site-directed mutagenesis. Thus, any host cells that have a certain level of homology with a GRAS host, for example at least 70% but preferably at least 80% and more preferably at least 90% homology with a GRAS host, and a recombinant enzyme that is expressed as an active form in the host and any host cells containing the enzyme are all included in the criteria of the present invention.

The present invention also provides a vector containing a gene encoding the arabinose isomerase of the present invention. The vector of the present invention is a typical vector for cloning or gene expression. The vector is not limited to a specific one and any vector known to those in the art is acceptable.

In the present invention, a promoter which is active in *Corynebacterium* was used as the vector to express a thermophilic isomerase as an active form. The promoter sequence used for the gene expression in the *Corynebacterium* has not been identified unlike other promoters used in industrial microorganisms such as *E. coli* or *Bacillus subtilis*. Herein, a strong promoter that originates from *Corynebacterium*, a popular industrial microorganism, and is able to be expressed in *E. coli* has been developed, Tac promoter is known as being one of the strongest promoters. Tac promoter is prepared by fusion of a sequence of the −35 region of the tryptophane operon promoter of *E. coli* with a sequence of the −10 region of the lactose operon promoter of *E. coli*. The promoter composed of CJ-1~CJ-7 in the present invention was confirmed to be more effective in expressing a target gene in *Corynebacterium* sp. bacteria cells than tac promoter (Korean Patent Publication No. 10-2006-0068505).

The *Corynebacterium* promoter of the present invention exhibits promoter activity not only in *Corynebacterium* sp. microorganisms, but also in *Escherichia* sp. bacteria and *E. coli* cells. In particular, the promoter of the present invention exhibits promoter activity in *Escherichia* sp. bacteria cells at least two times higher than tac promoter does.

The food grade strain, which means a GRAS strain, of the present invention includes *Corynebacterium*, and more specifically *Corynebacterium glutamicum* KCTC 10302.

According to an embodiment of the present invention, a recombinant strain was prepared by transforming *Corynebacterium* with the vector, which was then cultured to provide food grade arabinose isomerase. The culture medium and conditions depended on the kind of host.

The present invention provides a recombinant arabinose isomerase and a method of preparing tagatose from galactose by immobilizing host cells containing the recombinant enzyme.

BRIEF DESCRIPTION OF THE DRAWINGS

The application of the preferred embodiments of the present invention is best understood with reference to the accompanying drawings, wherein.

M: wide range protein marker (Bio-Rad, U.S.A)

1: crude enzyme solution

2: heat-treated enzyme supernatant 3. enzyme fragment after anion exchange chromatography (HiTrap Q column, GE Healthcare, U.S.A.)

4. purified enzyme fragment after size exclusion chromatography (Superdex 200 pg column, GE Healthcare, U.S.A.)

Figure 4:
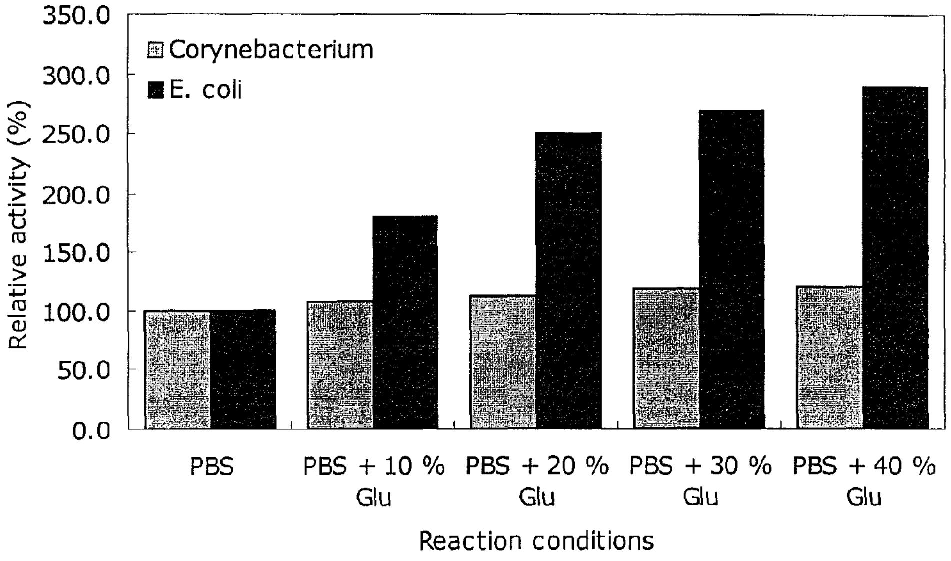

FIG. 4 is a graph illustrating the amount of the arabinose isomerase. The recombinant *Corynebacterium* and *E. coli* containing the arabinose isomerase expressed as an active form therein were reacted in PBS (phosphate-buffered saline) containing different galactose concentrations of 0, 10, 20, 30 and 40% for 2 hours at high temperature (70° C.) with stirring, and then the level of enzyme expression in the buffer was measured.

BEST MODE FOR CARRYING OUT THE INVENTION

Practical and presently preferred embodiments of the present invention are illustrated as shown in the following examples.

However, it will be appreciated that those skilled in the art, on consideration of this disclosure, may make modifications and improvements within the spirit and scope of the present invention.

EXAMPLES

In the preferred embodiment of the present invention, a gene encoding thermophilic arabinose isomerase originating from the hyperthermophile *Thermotoga neapolitana* DSM 5068 was inserted into pCJ-1 and pCJ-7 (*E. coli-Corynebacterium* shuttle vector, Korean Patent Publication No. 10-2006-0068505). *Corynebacterium glutamicum KCTC* 13032 was transfected with the above vectors, in which the said protein was finally over-expressed. The recombinant strains *Corynebacterium glutamicum* CJ-1-TNAI (KCCM10786P) and CJ-7-TNAI (KCCM10787P) were cultured and cell extracts were obtained from each stage of the cell culture. The production activity of tagatose was measured, that is the amount of active recombinant protein was measured stage by stage. The optimally expressed resultant culture was separated and purified by cell lysis, heat treatment, ion exchange resin and gel chromatography. Finally, the amino acid sequence of the amino-terminal was examined and the production activity of tagatose was confirmed by measurement of the protein activity.

Example 1

Cloning of the Arabinose Isomerase

*Thermotoga neapolitana* DSM 5068 was cultured under anaerobic conditions. Centrifugation was performed at 8,000× g for 10 minutes to recover the cultured cells. Genomic DNA was extracted from the obtained cells by using a Cell culture DNA Midi Kit (Qiagen, U.S.A.). Polymerase Chain Reaction (PCR) was performed with the genomic DNA by using oligonucleotides 5'-CCCGA TATCATGATC-GATCTCAAACAGTATGAG-3' (SEQ. ID. NO: 1) and 5'-TGCACTGCAGTCATCT TTTTAAAAGTCCCC-3' (SEQ. ID. NO: 2) with the insertion of EcoRV and PstI restriction enzyme site sequences as primers. PCR product was obtained by amplifying the 1509 bp DNA containing the *Thermotoga neapolitana* arabinose isomerase gene. To mass-produce the arabinose isomerase encoded by the amplified gene, two of the *Corynebacterium* sp. derived vectors exhibiting excellent protein-overexpressing capacity were selected. The vectors were introduced into *E. coli* DH5alpha, which were deposited at the Korean Culture Center of Microorganisms (KCCM), an international depository authority (IDA), on Nov. 6, 2004 (Accession Nos: KCCM-10611 and KCCM-10617) (Table 1).

TABLE 1

| Promoter | Vector | Accession No. | Derived Protein |
|---|---|---|---|
| pCJ1 | pECCG117 | KCCM-10611 | Heat shock protein hsp60 |
| pCJ7 | pECCG117 | KCCM-10617 | Manganese superoxide dismutase |

Figure 1:
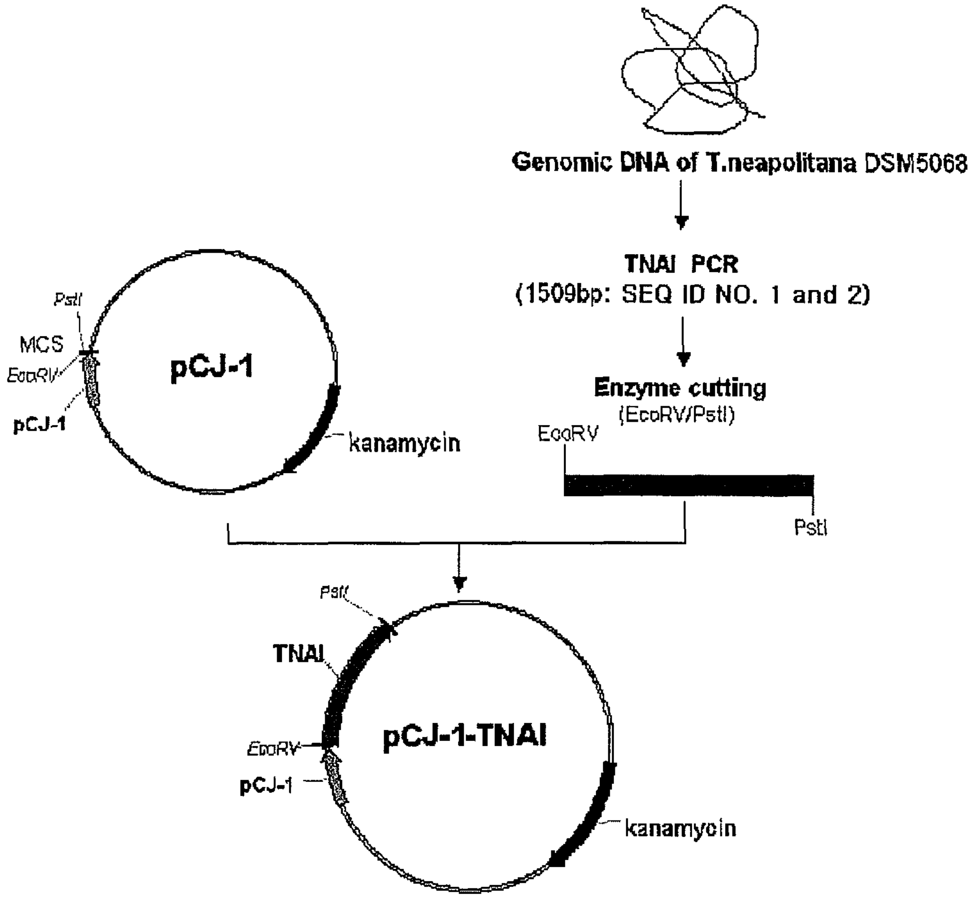
FIG. 1 is a schematic diagram illustrating the construction of the recombinant expression vectors pCJ-1-TNAI and pCJ-7-TNAI containing a gene encoding the thermophilic arabinose isomerase originating from the *Thermotoga neapolitana* DSM 5068 strain.

The PCR product digested with restriction enzymes EcoRV and PstI was inserted into the shuttle vectors pCJ-1 and pCJ-7, which were digested with the same enzymes, leading to the construction of the recombinant expression vectors pCJ-1-TNAI and pCJ-7-TNAI (see FIG. 1). *Corynebacterium glutamicum* KCTC 13032 was transfected with the recombinant expression vectors pCJ-1-TNAI and pCJ-7-TNAI to prepare recombinant strains, which were named *'Corynebacterium glutamicum CJ-*1-*TNAI'* and *'Corynebacterium glutamicum CJ-7-TNAI'*. The recombinant strains were deposited at the Korean Culture Center of Microorganisms (KCCM), an International Depositary Authority (IDA), addressed at #361-221, Hongje 1-Dong, Seodaemun-Gu, Seoul, Korea, on Oct. 18, 2006 (Accession Nos: KCCM10786P and KCCM10787P).

Example 2

Expression of the Arabinose Isomerase in *Corynebacterium*

The recombinant strains *Corynebacterium glutamicum* CJ-1-TNAI and *Corynebacterium glutamicum* CJ-7-TNAI (Accession Nos: KCCM10786P and KCCM10787P) prepared in Example 1 were inoculated in MB medium (Bacto-trypton 10 g/L, Bacto-yeast extract 5 g/L, NaCl 10 g/L, Soytone 5 g/L) containing 10 μg/Ml of kanamycin at the concentration of $OD_{600}$=0.1, followed by culture at 30° C. for 24 hours to induce expression of the recombinant arabinose isomerase. To measure the enzyme activity of the expressed arabinose isomerase, the culture solution was centrifuged at 8,000× g for 10 minutes and cells were recovered. The cells were resuspended in 50 mM Tris-HCl (pH 7.0) buffer, followed by ultrasonification to lyse the cells. The supernatant was obtained as a crude enzyme solution, with which galactose isomerization was performed. Particularly, for the isomerization, 100 μl of an enzyme solution containing 40 mM of galactose as a substrate was mixed with 1 ml of a reaction buffer (50 mM Tris-HCl, pH 7.0). At that time, 5 mM of $MnCl_2$ and 1mM of $CoCl_2$ were added to the reaction mixture. The crude enzyme reaction mixture was reacted at 60° C. for 20 minutes. The activity of the crude enzyme was measured by the cystein-carbazol-sulfuric acid method (Dische, Z., and E. Borenfreund., A New Spectrophotometric Method for the Detection and Determination of Keto Sugars and Trioses, *J. Biol. Chem.,* 192:583-587, 1951). The protein contained in the crude enzyme solution was quantified with a Bradford assay kit (Biorad, U.S.A.). As a result, the isomerase activity was 2.050 (mg-tagatose/mg-protein·h), indicating that the product of galactose isomerization, tagatose, was successfully generated.

Example 3

Optimization of the Culture Condition for Mass-Production of the Recombinant Strain The recombinant strains prepared in Example 2 were inoculated in MB medium (Bacto-trypton 10 g/L, Bacto-yeast extract 5 g/L, NaCl 10 g/L, Soytone 5 g/L) containing 10 μg/Ml of kanamycin at the primary concentration of $OD_{600}$=0.6. The growth of the strains in two basic media for the culture of *Corynebacterium*, MB medium (Bacto-trypton 10 g/L, Bacto-yeast extract 5 g/L, NaCl 10 g/L, Soytone 5 g/L) and a modified medium (Bacto-peptone 10 g/L, Bacto-yeast extract 5 g/L, NaCl 2.5 g/L, Beef extract 5 g/L), was investigated. Temperature dependent (25° C., 30° C., 37° C.), pH dependent, glucose (carbon source) and sucrose concentration dependent growths in the two media were compared. In addition, the growths under the various conditions and the expression levels of the enzyme thereby were measured every hour to judge the optimum expression condition for mass-production of the recombinant arabinose isomerase (Tables 2 and 3).

TABLE 2

| | Modified medium | MB medium | | | | |
|---|---|---|---|---|---|---|
| | Aerobic | Aerobic | Stationary | 25° C. | 30° C. | 37° C. |
| $OD_{600}$ | 10.1 | 9.4 | 5.56 | 8.88 | 10.1 | 4.44 |
| pH | 7.5 | 7.6 | 7.8 | 7.4 | 7.5 | 7.5 |
| Activity (mU/ml) | 60.907 | 56.09 | 34.2 | 58.783 | 60.907 | 29.054 |

TABLE 3

| | | Sucrose | | | | Glucose | | | |
|---|---|---|---|---|---|---|---|---|---|
| | 0% | 2.5% | 5% | 7.5% | 10% | 2.5% | 5% | 7.5% | 10% |
| $OD_{600}$ | 10.1 | 13.6 | 12.72 | 14.86 | 12.94 | 14.7 | 14.32 | 10.96 | 4.36 |
| pH | 7.5 | 4.5 | 4.7 | 4.7 | 4.7 | 4.5 | 4.5 | 4.7 | 4.7 |
| Activity (mU/ml) | 60.907 | 85.088 | 82.160 | 79.104 | 73.708 | 67.935 | 58.896 | 58.649 | 42.441 |

Figure 2:
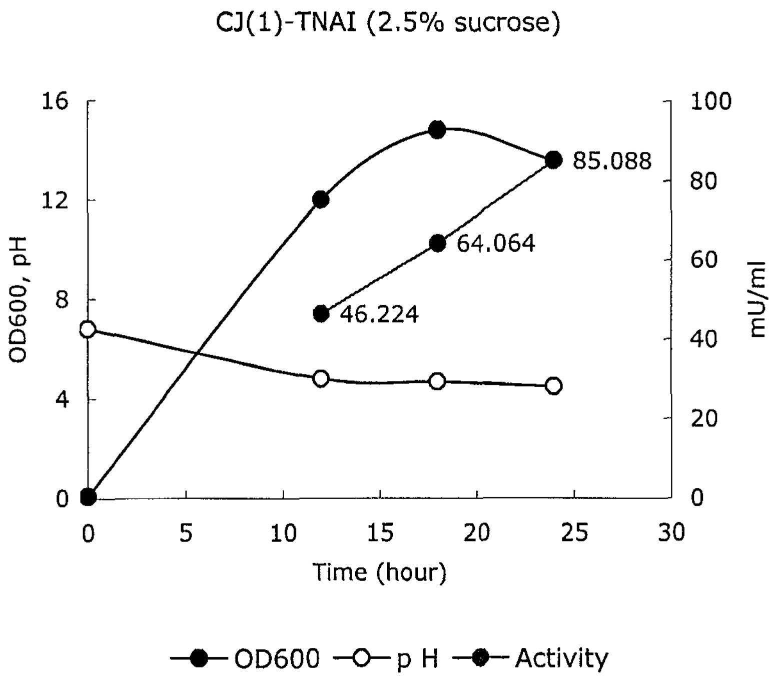
FIG. 2 is a graph illustrating the time dependent culture growth of the recombinant *Corynebacterium* strain. Particularly, the recombinant *Corynebacterium* was cultured in an optimum medium at 30° C. for 24 hours.

To measure the enzyme activity of the recombinant arabinose isomerase, the enzyme was treated and quantified in the same manner as described in Example 2. When cells were cultured at 30° C. under aerobic conditions with the addition of 2.5% sucrose, tagatose, the product of galactose isomerization, showed approximately 85.1 mU/ml of enzyme activity which is 1.4 times higher than that observed in the standard culture (60.9 mU/ml), suggesting that the enzyme activity increased with the increase in the growth of the cells. The cell growth results in the optimum medium are shown in FIG. 2.

Example 4

Figure 3:
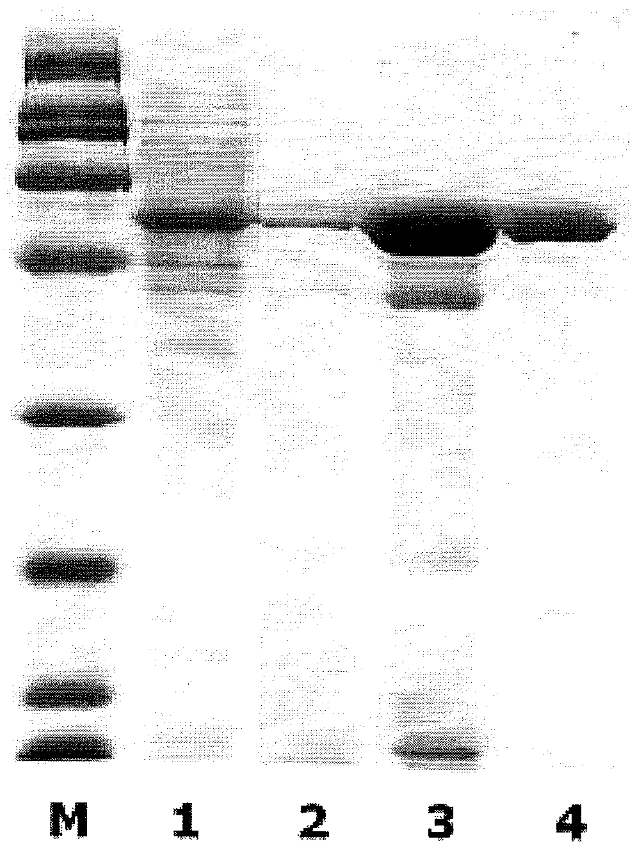
FIG. 3 is a photograph illustrating the results of SDS-PAGE (sodium dodecyl sulfate-polyacrylamide gel electrophoresis) of the total protein expression patterns observed in crude enzyme solutions of each step of separation and purification of the arabinose isomerase expressed from the recombinant *Corynebacterium*. Each protein band indicates as follows.

Separation and Purification of the Recombinant Arabinose Isomerase and Confirmation of the Expression of Active Protein by N-Terminal Amino Acid sequencing 2 L culture of the recombinant strain was performed under the optimum culture conditions determined in the above Example 3. The culture solution was centrifuged at 8000× g for 10 minutes and cells were recovered. The cells were resuspended in 50 mM Tris-HCl (pH 7.0) buffer, and used for the protein purification. The cell suspension progressed to cell lysis using a high pressure cell homogenizer T-series (4.0 kW; Constant systems, UK), followed by heat-treatment at 80° C. for 20 minutes. Centrifugation was performed at 10,000× g for 10 minutes to separate the expressed recombinant thermophilic arabinose isomerase. The separated recombinant enzyme solution was purified by anion-exchange chromatography (Hiprep Q 16/10, Amersham Bioscience, U.S.A.), ultrafiltration (Centriprep 30, Amicon, Germany) and size-exclusion chromatography; Superdex 200 pg, Amersham Bioscience, U.S.A.) (Table 4). The protein composition of the enzyme solution of each step was analyzed by SDS-PAGE (sodium dodecyl sulfate-polyacrylamide gel electrophoresis) (FIG. 3).

TABLE 4

| Purification stage | Total protein (mg) | Total activity (AU) | Purification (%) | Yield (%) |
|---|---|---|---|---|
| Crude enzyme solution | 665 | 410.4 | 1.0 | 100 |
| Heat treatment | 480 | 364.3 | 1.2 | 89 |
| Ion exchange chromatography | 63.5 | 201.5 | 5.1 | 49 |
| Gel chromatography | 28.1 | 136.3 | 7.7 | 33 |

The separated and purified recombinant protein was finally identified by N-terminal amino acid sequencing. The protein purified by gel chromatography was analyzed by SDS-PAGE and as a result, it was confirmed that the protein had a molecular weight of approximately 55 kDa, which was the same molecular weight as the *Thermotoga neapolitana* sp. arabinose isomerase. The protein band was transferred to a PVDF membrane for further investigation by the Korean Basic Science Institute. As a result, the 10 amino acids of the amino-terminal of the separated recombinant protein were identified as 'Met-Ile-Asp-Leu-Lys-Gln-Tyr-Glu-Phe-Trp' which was the sequence of the N-terminal protein sequence of *Thermotoga neapolitana* sp. arabinose isomerase. Therefore, this sequence was confirmed to be the same as the amino acid sequence of the arabinose isomerase originated from *Thermotoga neapolitana* sp. (SEQ. ID. NO: 3).

Example 5

Reaction Stability of the Recombinant Strain for Enzyme Expression at High Temperature and High Concentration

*Corynebacterium* is a highly stable strain under various production conditions and has a comparatively hard cell membrane, therefore it remains stable even under high osmotic conditions caused by a high concentration of sucrose. These characteristics of the strain favor the enhancement of reaction stability in high concentration of a substrate. Therefore taking advantage of such characteristics, the present inventors expressed hyperthermophilic arabinose isomerase in the *Corynebacterium*.

The recombinant *Corynebacterium* strain cultured in a medium prepared in Example 3 and the recombinant *E. coli* strain cultured in LB medium (5 g/L Yeast extract, 10 g/L Bacto-trypton, 10 g/L Sodium chloride) were centrifuged respectively at 8000× g for 10 minutes to obtain cells. The cells were resuspended in PBS (phosphate buffered saline) for further experiments. To compare the strain stability at high substrate concentration, 0, 10, 20, 30 and 40% galactose were added to the solution, followed by reaction with stirring at 70° C. for 0, 1, and 2 hours. To quantify the protein expressed in the cells of each reaction product, centrifugation was performed at 13,000× g for 10 minutes and the supernatant was obtained. Then, the expressed proteins were quantified by BCA (bicinchonic acid protein assay method). From the comparison of the protein expression according to the substrate concentration between the recombinant *E. coli* cells and the recombinant *Corynebacterium* cells, it was confirmed that the level of protein expression in *Corynebacterium* was significantly lower, compared with that in the control *E. coli*. In the recombinant *E. coli*, the concentration of galactose was significantly increased as the reaction went on, whereas the expression of the protein in *Corynebacterium* increased approximately 20% even after starting with the highest galactose concentration of this experiment which was 40% (FIG. 4).

The above results indicate that the protein elution is remarkably reduced in the cells under the high substrate concentration, compared to that in *E. coli*. That is, unlike the conventional *E. coli* host, a *Corynebacterium* host containing the enzyme expressed therein exhibits reduced elution of intracellular protein under high sugar content.

*Corynebacterium* host was also confirmed to be very stable under tough reaction conditions including high temperature and high substrate concentration, compared with the *E. coli* host. This stability favors the increase of reaction stability in a cell immobilized reactor and thus results in the increase of the half-life of the cell immobilized reactor.

INDUSTRIAL APPLICABILITY

As explained hereinbefore, the stable expression of arabinose isomerase originating from the hyperthermophile *Thermotoga* sp. was observed in *Corynebacterium*, and thus immobilized continuous reaction was efficiently carried out in the preferred embodiment of the present invention by using the *Corynebacterium* containing the active form of the enzyme. To produce biotechnical food material using a microorganism enzyme, an additive must meet a GRAS food grade. The arabinose isomerase originating from the food grade *Thermotoga* sp. prepared by the method of the present invention can be applied to a continuous reaction stably to increase the possibility of industrialization of the enzyme.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A method for producing an arabinose isomerase comprising the steps of:

preparing a recombinant vector by inserting a gene encoding a thermophilic arabinose isomerase, which has the amino acid sequence of SEQ ID NO:3 originating from the *Thermotoga neapolitana* DSM 5068, into the shuttle vector pCJ-1(KCCM 10611) or pCJ-7(KCCM 10617);

transfecting a *Corynebacterium* sp. strain with the recombinant vector; and producing the arabinose isomerase by culturing the *Corynebacterium* sp. strain.

2. The method according to claim 1, wherein the strain is *Corynebacterium glutamicum* CJ-1-TNAI (KCCM 10786P).

3. The method according to claim 1, wherein the strain is *Corynebacterium glutamicum* CJ-7-TNAI (KCCM 10787P).

* * * * *

SEQUENCE LISTING

<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: primer 1

<400> SEQUENCE: 1
cccgatatca tgatcgatct caaacagtat gag 33

<210> SEQ ID NO 2
<211> LENGTH: 30
<212> TYPE: DNA
<213> ORGANISM: Artificial Sequence
<220> FEATURE:
<223> OTHER INFORMATION: primer 2

<400> SEQUENCE: 2
tgcactgcag tcatcttttt aaaagtcccc 30

<210> SEQ ID NO 3
<211> LENGTH: 496
<212> TYPE: PRT
<213> ORGANISM: Corynebacterium glutamicum

<400> SEQUENCE: 3

Met Ile Asp Leu Lys Gln Tyr Glu Phe Trp Phe Leu Val Gly Ser Gln
1 5 10 15

Tyr Leu Tyr Gly Leu Glu Thr Leu Lys Lys Val Glu Gln Gln Ala Ser
20 25 30

Arg Ile Val Glu Ala Leu Asn Asn Asp Pro Ile Phe Pro Ser Lys Ile
35 40 45

Val Leu Lys Pro Val Leu Lys Asn Ser Ala Glu Ile Arg Glu Ile Phe
50 55 60

Glu Lys Ala Asn Ala Glu Pro Lys Cys Ala Gly Val Ile Val Trp Met
65 70 75 80

His Thr Phe Ser Pro Ser Lys Met Trp Ile Arg Gly Leu Ser Ile Asn
85 90 95

Lys Lys Pro Leu Leu His Leu His Thr Gln Tyr Asn Arg Glu Ile Pro
100 105 110

Trp Asp Thr Ile Asp Met Asp Tyr Met Asn Leu Asn Gln Ser Ala His
115 120 125

Gly Asp Arg Glu His Gly Phe Ile His Ala Arg Met Arg Leu Pro Arg
130 135 140

Lys Val Val Val Gly His Trp Glu Asp Arg Glu Val Arg Glu Lys Ile
145 150 155 160

Ala Lys Trp Met Arg Val Ala Cys Ala Ile Gln Asp Gly Arg Thr Gly
165 170 175

Gln Ile Val Arg Phe Gly Asp Asn Met Arg Glu Val Ala Ser Thr Glu
180 185 190

Asp Asp Lys Val Glu Ala Gln Ile Lys Leu Gly Trp Ser Ile Asn Thr
195 200 205

-continued

```
Trp Gly Val Gly Glu Leu Ala Glu Gly Val Lys Ala Val Pro Glu Asn
    210                 215                 220

Glu Val Glu Glu Leu Leu Lys Glu Tyr Lys Glu Arg Tyr Ile Met Pro
225                 230                 235                 240

Glu Asp Glu Tyr Ser Leu Lys Ala Ile Arg Glu Gln Ala Lys Met Glu
                245                 250                 255

Ile Ala Leu Arg Glu Phe Leu Lys Glu Lys Asn Ala Ile Ala Phe Thr
            260                 265                 270

Thr Thr Phe Glu Asp Leu His Asp Leu Pro Gln Leu Pro Gly Leu Ala
        275                 280                 285

Val Gln Arg Leu Met Glu Glu Gly Tyr Gly Phe Gly Ala Glu Gly Asp
    290                 295                 300

Trp Lys Ala Ala Gly Leu Val Arg Ala Leu Lys Val Met Gly Ala Gly
305                 310                 315                 320

Leu Pro Gly Gly Thr Ser Phe Met Glu Asp Tyr Thr Tyr His Leu Thr
                325                 330                 335

Pro Gly Asn Glu Leu Val Leu Gly Ala His Met Leu Glu Val Cys Pro
            340                 345                 350

Thr Ile Ala Lys Glu Lys Pro Arg Ile Glu Val His Pro Leu Ser Ile
        355                 360                 365

Gly Gly Lys Ala Asp Pro Ala Arg Leu Val Phe Asp Gly Gln Glu Gly
    370                 375                 380

Pro Ala Val Asn Ala Ser Ile Val Asp Met Gly Asn Arg Phe Arg Leu
385                 390                 395                 400

Val Val Asn Arg Val Leu Ser Val Pro Ile Glu Arg Lys Met Pro Lys
                405                 410                 415

Leu Pro Thr Ala Arg Val Leu Trp Lys Pro Leu Pro Asp Phe Lys Arg
            420                 425                 430

Ala Thr Thr Ala Trp Ile Leu Ala Gly Gly Ser His His Thr Ala Phe
        435                 440                 445

Ser Thr Ala Val Asp Val Glu Tyr Leu Ile Asp Trp Ala Glu Ala Leu
    450                 455                 460

Glu Ile Glu Tyr Leu Val Ile Asp Glu Asn Leu Asp Leu Glu Asn Phe
465                 470                 475                 480

Lys Lys Glu Leu Arg Trp Asn Glu Leu Tyr Trp Gly Leu Leu Lys Arg
                485                 490                 495
```